United States Patent
Sughrue et al.

(10) Patent No.: US 11,399,757 B1
(45) Date of Patent: Aug. 2, 2022

(54) MEDICAL IMAGING WITH FEATURES TO DETERMINE EMOTIONAL STATE

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/378,648

(22) Filed: Jul. 16, 2021

(51) Int. Cl.
*A61B 5/05* (2021.01)
*A61B 5/16* (2006.01)
*G16H 30/20* (2018.01)
*G16H 30/40* (2018.01)
*G16H 50/20* (2018.01)
*G06T 7/00* (2017.01)
*A61B 5/026* (2006.01)
(Continued)

(52) U.S. Cl.
CPC .......... *A61B 5/165* (2013.01); *A61B 5/0263* (2013.01); *A61B 5/4064* (2013.01); *G01R 33/4806* (2013.01); *G01R 33/5608* (2013.01); *G06T 7/0012* (2013.01); *G16H 30/20* (2018.01); *G16H 30/40* (2018.01); *G16H 50/20* (2018.01); *G06T 2207/10016* (2013.01); *G06T 2207/10088* (2013.01); *G06T 2207/30016* (2013.01); *G16H 20/10* (2018.01); *G16H 20/70* (2018.01)

(58) Field of Classification Search
CPC ..... A61B 5/165; A61B 5/4064; A61B 5/0263; G01R 33/4806; G01R 33/5608; G16H 30/20; G16H 30/40
See application file for complete search history.

(56) References Cited

U.S. PATENT DOCUMENTS 10,586,326 B2   3/2020   Solbersweig et al.
10,874,340 B2   12/2020  Rau et al.
(Continued)

OTHER PUBLICATIONS

Horikawa et al., "The neural representation of emotion is high-dimensional, categorical, anddistributed across transmodal brain regions" Department of Neuroinformatics, ATR Computational Neuroscience Laboratories. Dec. 11, 2019, 60 pages.
(Continued)

*Primary Examiner* — Joel F Brutus
(74) *Attorney, Agent, or Firm* — Fish & Richardson P.C.

(57) ABSTRACT fMRI data of a subject brain is accessed and may include a plurality of time-sequenced volumetric images of activity in a subject brain. A plurality of emotion vectors are accessed, each emotion vector tagged with a specified emotional state. From the fMRI data and using the emotion vectors, a plurality of fMRI state vectors are determined at various points in time, where each fMRI state vector is a combination of the emotion vectors and represents the state of the subject brain at a particular point in time. Flow data is determined to identify a trajectory, over time, of the subject brain as reflected by the fMRI data, through a state space defined by the emotion vectors, where the flow data is based at least in part on the fMRI vectors at various points in time. From the flow data, data is generated that shows changes, through time, in at least one emotional state of the brain.

20 Claims, 5 Drawing Sheets

(51) Int. Cl.
  *G01R 33/48*   (2006.01)
  *G01R 33/56*   (2006.01)
  *A61B 5/00*    (2006.01)
  *G16H 20/10*       (2018.01)
  *G16H 20/70*       (2018.01)

(56) References Cited

U.S. PATENT DOCUMENTS

| | | | | |
|---|---|---|---|---|
| 2012/0179003 A1* | 7/2012 | Faber | ............... | A61B 5/4064 |
| | | | | 600/300 |
| 2015/0339363 A1* | 11/2015 | Moldoveanu | ......... | G06F 3/0482 |
| | | | | 707/723 |
| 2019/0102511 A1 | 4/2019 | Murray et al. | | |
| 2019/0213761 A1 | 7/2019 | Rosen et al. | | |

OTHER PUBLICATIONS

Jirsa, "Structured Flows on Manifolds as guiding concepts in brain science," Hal Archives-ouvertes, dated Apr. 8, 2020, 15 pages.

Shine et al., "The low dimensional dynamic and integrative core of cognition in the human brain," The University of Sydney, Feb. 18, 2018, 33 pages.

* cited by examiner

MEDICAL IMAGING WITH FEATURES TO DETERMINE EMOTIONAL STATE

TECHNICAL FIELD

This specification relates to brain imaging and analysis of brain images.

BACKGROUND

Medical imaging includes the technique and process of creating visual representations of the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging also establishes a database of normal anatomy and physiology to make it possible to identify abnormalities.

SUMMARY

This specification describes technologies for generating information about a subject's emotional states based on brain imaging. These technologies generally involve scanning a subject's brain to generate a time series such as functional magnetic resonance imaging (fMRI) data. Then, that fMRI data can be analyzed and compared to data that describes brain activity associated with known emotions. From this analysis, a current emotional state for the subject can be found, as well as data defining transitions from one state to another. In some cases, these states may be defined by a weighted mix of various emotional states, and the movement through emotional states can define movement through a manifold space with dimensions matching the emotional states.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a system for generating diagnostic data from medical imaging, one or more computers and one or more storage devices on which are stored instructions that are operable, when executed by the one or more computers, to cause the one or more computers to perform operations that can include accessing fMRI data of a subject brain including a plurality of time-sequenced volumetric activity data for a subject brain. The operations also include accessing a plurality of emotion vectors, each emotion vector tagged with a specified emotional state. An emotion vector can be thought of as representing a mental state of a specific kind corresponding to a physiological state and/or a psychological state. In many cases, such a mental state can be surfaced in a subject by exposing the subject to known stimuli.

The operations also include determining, from the fMRI data and using the emotion vectors, a plurality of fMRI state vectors at various points in time, where each fMRI state vector is a combination of the emotion vectors and represents the state of the subject brain at a particular point in time. The operations also include determining flow data to identify a trajectory, over time, of the subject brain as reflected by the fMRI data, through a state space defined by the emotion vectors, where the flow data is based at least in part on the fMRI vectors at various points in time. The operations also include generating, from the flow data, data that shows changes, through time, in at least one emotional state of the brain. Other embodiments of this aspect include corresponding computer systems, apparatus, and computer programs recorded on one or more computer storage devices, each configured to perform the actions of the methods.

For a system of one or more computers to be configured to perform particular operations or actions means that the system has installed on it software, firmware, hardware, or a combination of them that in operation cause the system to perform the operations or actions. Similarly, for one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. In particular, one embodiment includes all the following features in combination. The operations may include accessing records of stimuli provided to the subject while the fMRI data was collected; and recording, in the diagnostic data, correspondences between provision of stimuli and the changes in emotional state in the brain. The operations may include selecting one of the stimuli for future exposure to the subject based on the recorded correspondences. The operations may include recording in the diagnostic data a resting emotional state for the subject based on the changes in emotional state of the brain. The operations may include providing the diagnostic data to a recommendation engine configured to receive the diagnostic data and provide one or more recommendations for interventions for the subject. The recommendation is one of the group including a drug intervention, and a behavioral intervention (e.g., verbal counseling of an individual to help build habits to improve the individual's health). The plurality of emotion vectors can include thirty-four emotion vectors. The emotion vectors can be labelled according to the stimuli that produce the vectors. The labels can include sexual desire, aesthetic appreciation, entrancement, disgust, amusement, fear, interest, anxiety, surprise, joy, horror, adoration, calmness, romance, awe, nostalgia, empathic pain, relief, awkwardness, craving, excitement, sadness, boredom, triumph, sympathy, admiration, anger, satisfaction, confusion, disappointment, pride, envy, contempt, and guilt. In certain embodiments, each emotion vector can store values reflecting average brain activity for other brains that have experienced the specified emotional state. Implementations of the described techniques may include hardware, a method or process, or computer software on a computer-accessible medium.

The subject matter described in this specification can be implemented in particular embodiments so as to realize one or more of the following advantages. Brain imaging is advanced. For example, the technology describe here can be used to generate objective measure of emotions of a subject, and changes to emotional state in time. This technology can aid clinical interventions by allowing a clinician to see measures of emotions in response to treatments or other stimuli. This technology can create quantitative visualization of emotional states during a time course statistically separated from the rest of the non-emotional state features in a data set. Unlike other approaches which do not process the data in a way which both is free from confounding from other aspects of influence, this technology can provide information this is more objective, less bias, and thus usable in a wider range of applications.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Emotional state and emotional state changes of a subject (e.g., a human or other animal) can be sensed using imaging of the subject's brain. For example, volumetric images of the brain over time can be examined to identify a mix of emotional contributors that combine to define the emotional state at each time. These contributors can be tracked over time to identify how the subject's emotional state changes over time.

Figure 1:
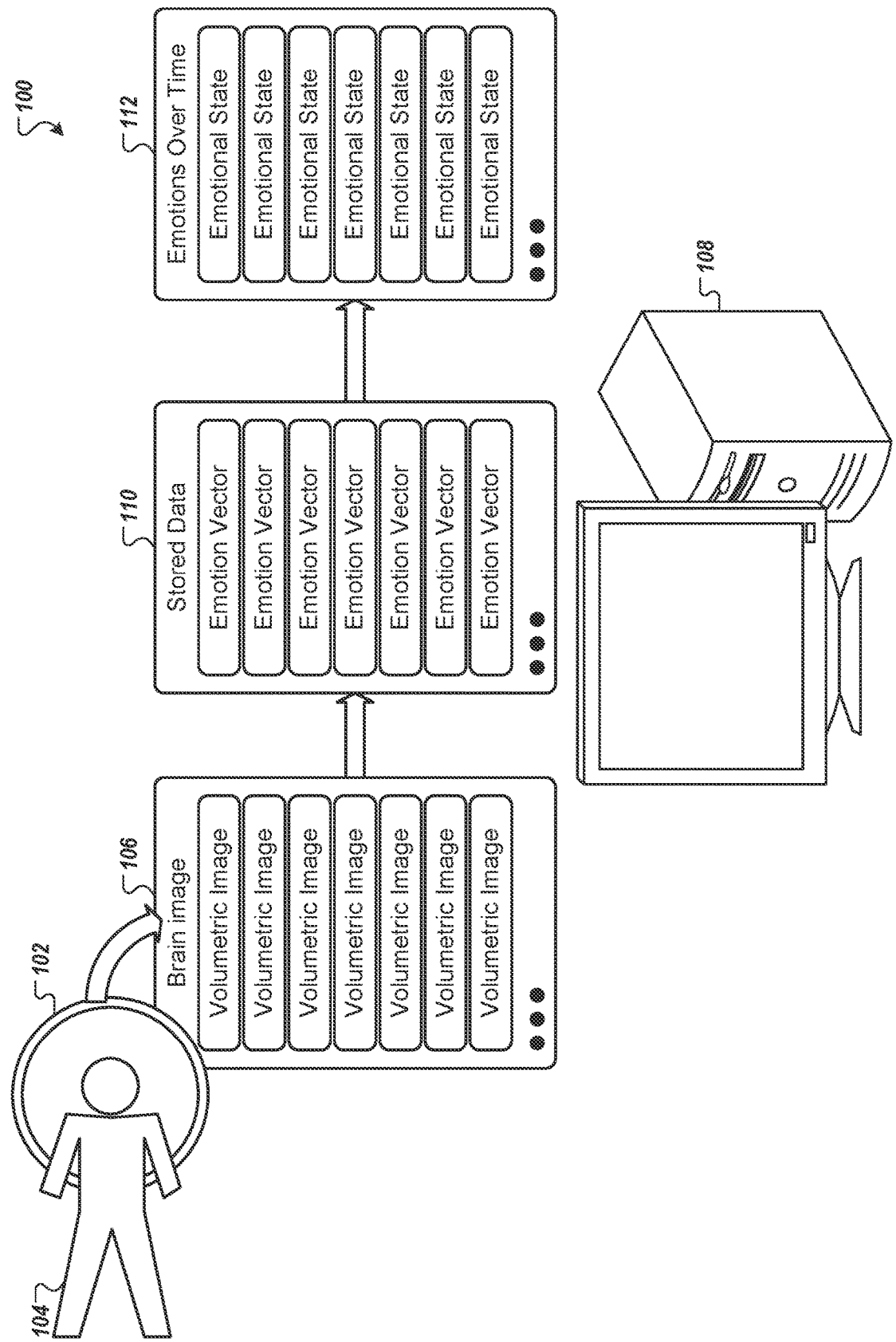
FIG. 1 is a diagram of a system that generates information about a subject's emotional state.

FIG. 1 is a diagram of a system 100 that generates information about a subject's emotional state. In the system 110, an imager 102 images a subject 104 to generate brain image data 106. A computer system 108 analyses the brain image data 106 with stored data 110 in order to generate data 112 about emotional states over time of the subject 104.

When the imager 102 generates the brain image data 106, the imager may perform, for example, fMRI imaging to create a sequence of volumetric "images" of the subject's 104 brain. These volumetric "images" can record data about both the relatively static shape of the brain as well as the relatively dynamic electrical activity of the brain.

The stored data 110 can include emotion vectors that each record data about brain activity when a subject is experiencing a particular emotional state. As will be appreciated the emotion vectors 110 can be generated by imaging many subject's brains while the subjects are experiencing the associated emotion. This training data may then be aggregated to find common functional data across the training data and recorded in the emotion vectors of data 110.

For each of the volumetric images of the brain data 106, a corresponding emotional state can be generated by the computer system 108 and stored in the data 112. For example, the computer system 108 can compare the first volumetric image, assigned a time value of 0, with each of the emotion vectors and record a resulting emotion state at time value 0. Then, the next volumetric image at time value 1 can be similarly examined and a corresponding emotional state can be stored in the data 112.

In this way, not only can emotional state be determined and recorded, but so to can changes in emotional state over time be determined and recorded. By using the emotion vectors to define an emotion-space, each emotion state can be mapped to a single point in the emotion space. This emotion-space may be high dimension (e.g., greater than three dimensions) and manifold (e.g., locally similar to Euclidean space near each point). In using such a space, the movement of the points through the emotion space may describe changes in the subject's 102 emotions. As these points move through a manifold in the space, predictions can be made about future locations of the emotional state. For example, a range of possible emotions may be identified by modeling a speed, acceleration, and orientation in the manifold, and projecting where a point will move to after a second, minute, etc. In this way, predictions of future emotional states may be generated. Similarly, a stimuli can be provided to the subject, and the movement of their emotional state can be compared to the projected emotional state, and a difference assigned to the stimuli.

One example use of this technology for a subject is described. The subject 102 may be suffering from a cognitive bias where they feel a high degree of fear of public speaking relative to an average person. In order to help this subject, a clinician may prescribe exposure therapy in which the subject becomes exposed to small amounts of their fear stimulus and learns they do not need to fear that stimulus. Once the small amount of stimulus is acceptable to the subject, greater levels of the stimulus may be exposed to the subject.

To begin, the subject 102 is imaged while speaking with the clinician. The clinician uses the system 100 to determine a 'base' emotional state for the subject, which can include a mix of fear and other emotions. The clinician can then speak with the subject, receive consent to begin the exposure therapy, and tell the subject to think about speaking in front of two members of the subject's family about a song the subject enjoys. The subject continues to be imaged and emotional state data continues to be generated. If the emotional state data shows an increase in fear, the clinician can ask the subject to modify the thought experiment to speaking only to one family member. However, if the emotional state data does not show an increase in fear, the clinician can ask the subject to continue to visualize the thought experiment and describe the visualization. If the subject's emotional state still does not show an increase in fear, the clinician can ask the subject to change the setting in a way that increases the stimulus, and can continue to modify the exercise based on the data 112. As will be appreciated, other uses of the system 100 are possible, including both clinical and non-clinical uses.

Figure 2:
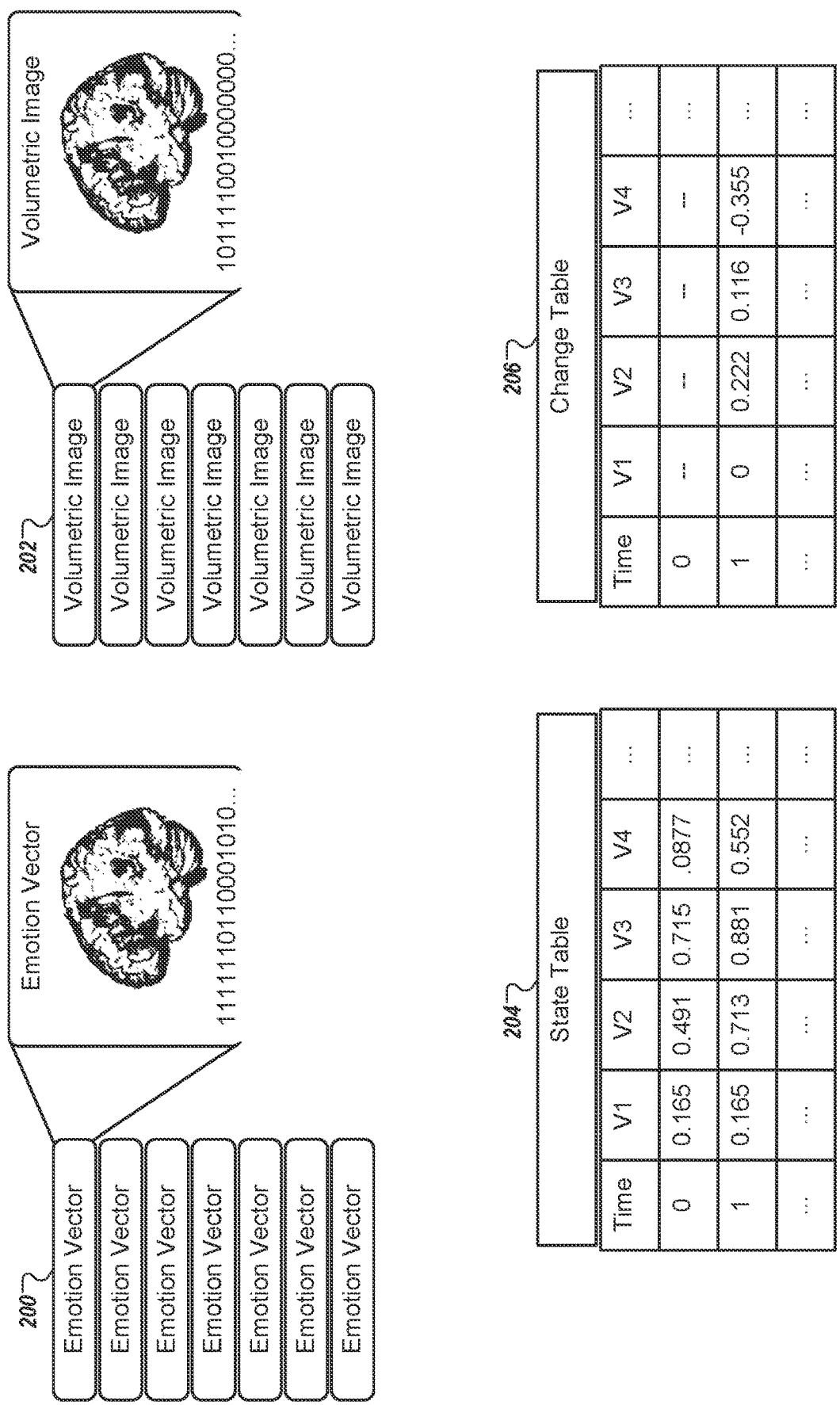
FIGS. 2 and 3 show example data that can be used when generating information about a subject's emotional state.

FIG. 2 shows example data that can be used when generating information about a subject's emotional state. For example, the data shown here may be used in the system 100.

Primary/Base emotion vectors 200 each store data about a brain's functional state when the subject of the brain is experiencing a particular primary/base emotion. It is believed that emotional states are a combination of physiological phenomena as well as psychological phenomena. As such, the functional state of the brain, as captured by an fMRI or other imaging process, can record sufficient data to uniquely identify a functional state that corresponds to specified emotion(s).

In some cases, emotional states can be treated as a weighted mix of a specific set of primary/base emotions. In such cases, most or all images of a brain will show functional state data that reflects a mix of the primary/base emotion vectors. These primary/base emotion vectors may be disentangled from each other, for example, by performing principal component analysis on recordings of the mixed emotional state data. In such cases, one emotion vector 200 may be generated and recorded for each of a set of primary emotional states, e.g., recorded when a subject is exposed to specific stimuli known to elicit a specific emotional response. Each of the vectors 200 can record data in binary format on a computer disk that can be interpreted as, for example, an array of numeric values, ascii characters, rendered as an image, or in another format or formats depending on the needs of the system 100. In some cases, the array of numeric values can correspond to relative blood-oxygen-level-dependent (BOLD) signal binned relative to the maximum and minima of those areas.

Each of the vectors 200 can be tagged with a specific emotional state. For example, the first emotion vector 200 can be tagged with fear, the second emotion vector 200 can be tagged with aesthetic appreciation, etc. The emotion vector 200 can then record values reflecting average brain activity for brains (e.g., brains other than the subject's 102 brain) that have experienced the specified emotional state. This data may include an image itself, and/or may include a set of data that is generated from the image. For example, the vectors 200 may include a cell for each parcelation in a brain parcelation map and may record a numeric value describing the activity of that parcelation as recorded, for example, as a BOLD signal detected via magnetic signal variation. In some cases, the emotion vector 200 may include less data than a full brain image.

In one scheme, there may be thirty-four emotion vectors 200, those being sexual desire, aesthetic appreciation, entrancement, disgust, amusement, fear, interest, anxiety, surprise, joy, horror, adoration, calmness, romance, awe, nostalgia, empathic pain, relief, awkwardness, craving, excitement, sadness, boredom, triumph, sympathy, admiration, anger, satisfaction, confusion, disappointment, pride, envy, contempt, and guilt. However, more, fewer, or different vectors may be used.

Volumetric images 202 include volumetric images recorded of the subject's 102 brain at sequential time periods. For example, an fMRI imaging system can image a subject's 102 brain. The image can record a three-dimensional (3D) image of the brain, and can combine the 3D images to create a four-dimensional (4D) image of the brain that shows the state of the subject's brain over time. Each of the volumetric images 202 can record data in binary format on a computer disk that can be interpreted as, for example, an array of numeric values, ascii characters, rendered as an image, or in another format or formats depending on the needs of the system 100.

A state table 204 can record emotional states of the subject 102 over time based on, for example, the emotion vectors 200 and the volumetric images 202. As shown, at various time points, values for $V_1, V_2, V_3, V_4 \ldots$ may be stored. The values for $V_N$ can record a weighted contribution that corresponding emotion vectors 200 contribute to the emotional state of the subject at the given time. In this example, the weight is recorded as a number from 0 to 1 recorded to three decimal places, however other data formats can be used. As shown here, $V_N$ values closer to 1 record emotional states that more heavily incorporate the emotion of the corresponding emotion vector, and $V_N$ values closer to 0 record emotional states that have little contribution from the corresponding emotion vector.

A change table 206 can record changes in emotional state of the subject 102 over time based on, for example, the state table 204. In this example change table 206, each row shows a change value that records the level of change of a particular $V_N$ compared to the time period directly previous. In this example, $V_1$ changed from 0.165 to 0.165, resulting in a value of 0 recorded in the change table 206. Similarly, $V_2$ changed from 0.491 to 0.713, resulting in a change value of 0.221 recorded in the change table 206. This show that the subject had no change in the emotion of $V_1$ and an increase in the emotion of $V_2$. As will be understood, positive values indicate an increase in the corresponding emotion and negative values indicate a decrease in the corresponding value.

Other formats of the tables are possible. For example, instead of recording a change compared to the previous time point, a change table 206 can record a change compared to an initial or base emotion for the subject 102. Such a table can be useful, for example, to show net change over a long period of time, where the moment-to-moment changes which may be more noisy, are less useful.

Figure 3:
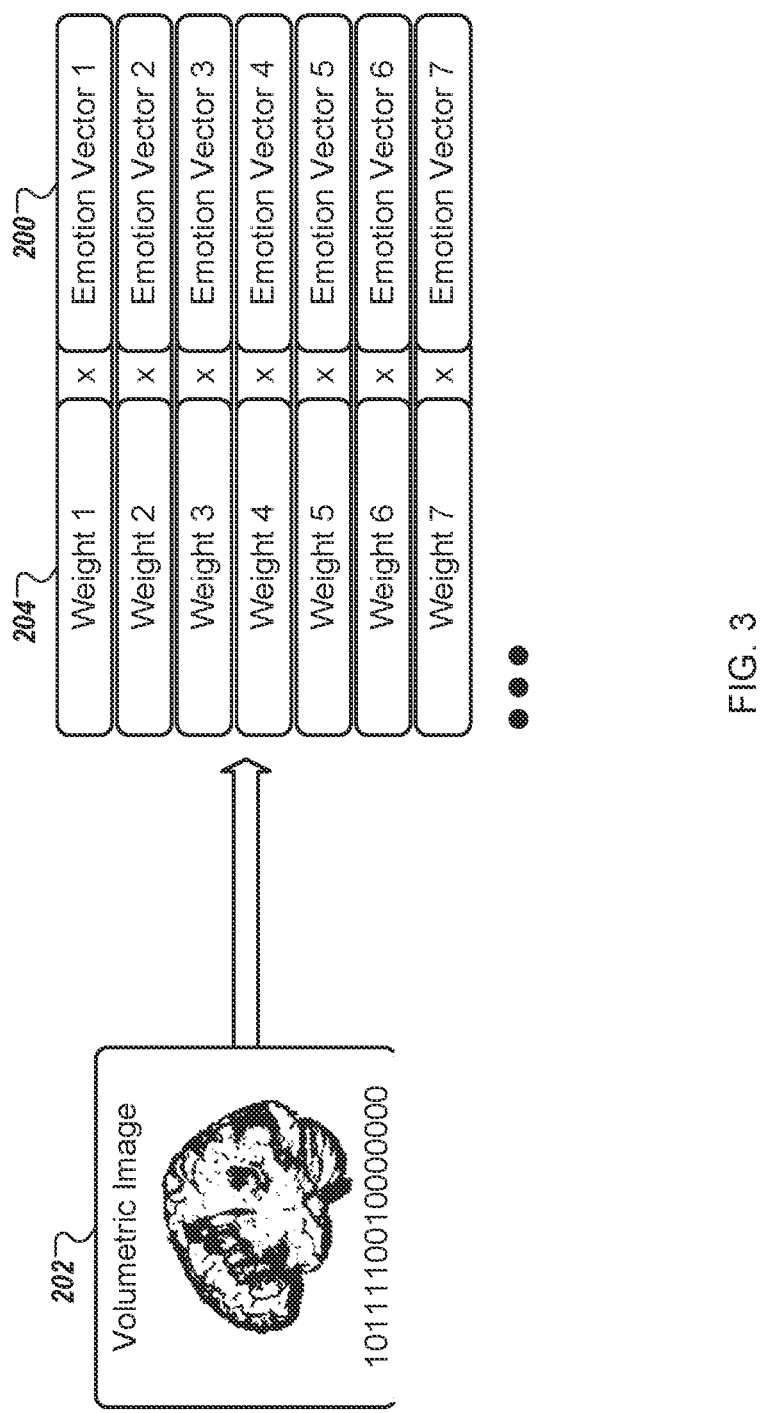

FIG. 3 shows the data 200-204 in a schematic arrangement to show the relationships between volumetric images 202, state table 204, and emotion vectors 200. As shown here, a single volumetric image 202 has associated a plurality of weights 204, which are associated with (e.g., multiplied by elements of) a corresponding emotion vector 200. Another volumetric image (not shown) would also have another sequence of weights associated for the same emotion vectors 200.

Figure 4:
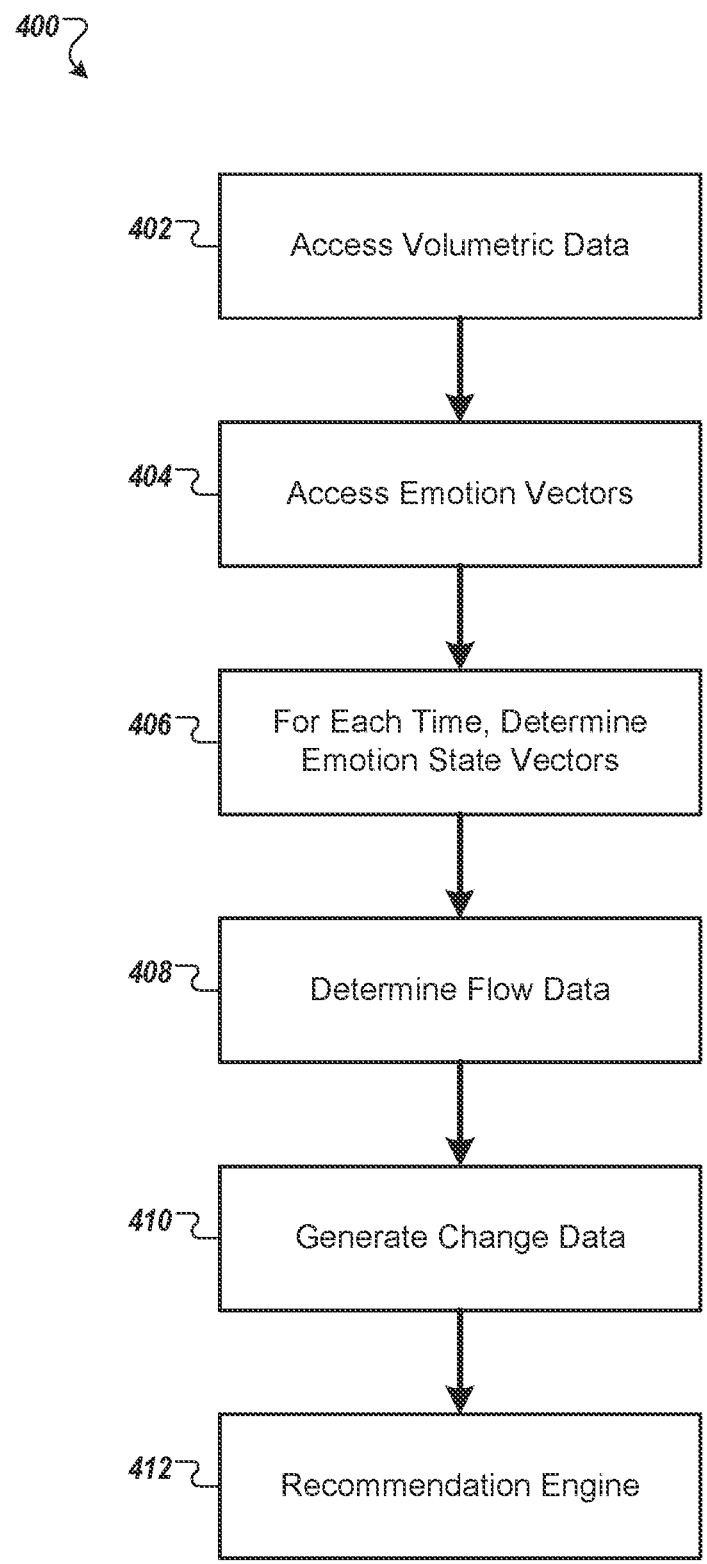
FIG. 4 shows an example process for generating information about a subject's emotional state.

FIG. 4 shows an example process 400 for generating information about a subject's emotional state. The process 400 may be used, for example, by the computer system 108 in generating the data 204 and 206. However, other systems may be used to perform the process 400 and other similar processes.

fMRI data of a subject brain is accessed 402. The data includes a plurality of time-sequenced volumetric images of activity in a subject brain. For example, the imager 102 can capture an fMRI of a human subject 104 and provide volumetric images 202 based on the fMRI data to the computer 108. A plurality of emotion vectors are accessed 404. For example, the computer system 108 can access the emotion vectors 200 from long-term memory and load the emotion vectors 200 into short-term memory for usage in the process 400.

From the fMRI data and using the emotion vectors, a plurality of fMRI state vectors at various points in time are determined 406. For example, the computer system 108 can analyze each of the volumetric images 202. This analysis may be performed in parallel, in sequence, or in a combination of the two. Each volumetric image 202 can be mapped into a space defined by the emotion vectors to place a point in a manifold (e.g., a collection of points forming a certain kind of set, such as those of a topologically closed surface or an analog of this in three or more dimensions) based on the contribution of each emotion vector 200 to the volumetric image 202. This analysis can create the state table 204 previously described, or another data structure.

Flow data is determined to identify a trajectory, over time, of the subject brain as reflected by the fMRI data, through a state space defined by the emotion vectors, wherein the flow data is based at least in part on the fMRI vectors at various points in time 408. For example, the computer system 108 can generate the change table 206 to record how the volumetric images 202, and thus the subject's emotional state, change over time. This change table 206 can record a flow of the subject's emotional state over the manifold depending on the emotional change.

Data that shows changes, through time, in at least one emotional state of the brain is generated from the flow data 410. For example, a graphic user interface may be rendered that graphically shows the changes in emotion. For example, a brain rendering may be shown with various colors gaining or losing intensity as the weight of an emotion vector increases or decreases. In another example, a report showing the top M emotions at each time may be generated.

A resting emotional state for the subject is recorded in diagnostic data based on the changes in emotional state of the brain. In some cases, a first emotional state, or an emotional state recorded when minimal stimulus is provided may be recorded as a resting emotional state. This can allow, for example, for a comparison with a given emotional state at any time point to determine how a subject's emotions are being influenced by stimulus.

The diagnostic data is provided to a recommendation engine configured to receive the diagnostic data and provide one or more recommendations for potential interventions for the subject 412. For example, the recommendation engine may provide to a clinician one or more possible courses of treatment for the subject based on the subject's measured emotional state. The clinician may then accept, reject, or modify one of those suggestions based on their clinical expertise. The recommendation may be a drug intervention, a behavioral intervention, transcranial magnetic stimulation, neurosurgery and/or other appropriate intervention.

Figure 5:
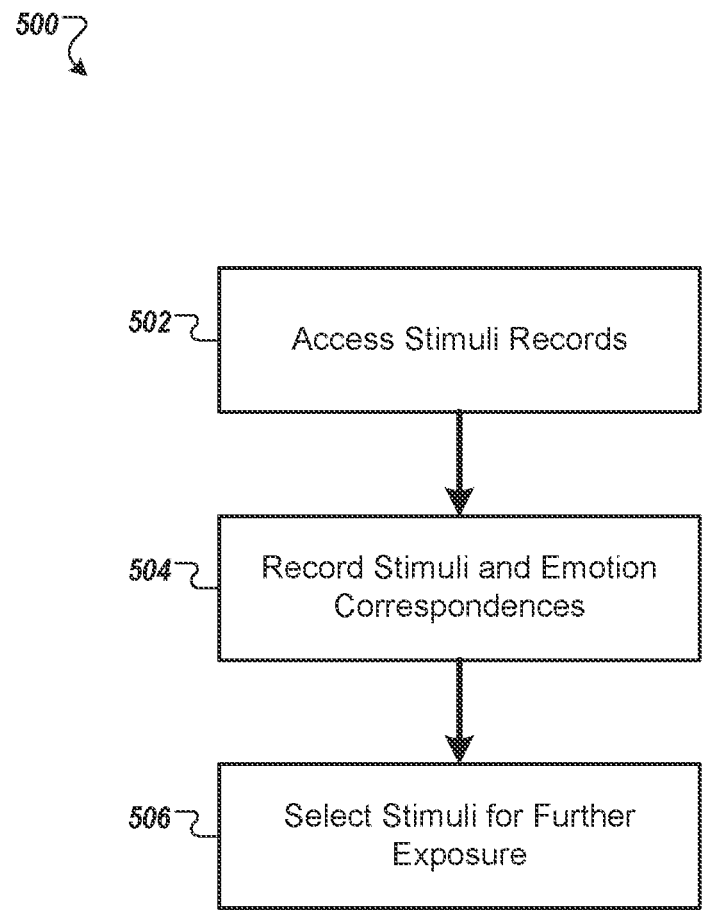
FIG. 5 shows an example process for providing stimuli to a subject.

FIG. 5 shows an example process for providing stimuli to a subject. The process 500 may be used, for example, by the computer system 108. However, other systems may be used to perform the process 500 and other similar processes.

The process 500 can be used to monitor a subject while providing a stimuli to the subject. With the process 500, for example, a clinician can provide treatment to a patient that is modulated based on the emotional response of the patient. In another example, a researcher can use the process 500 while investigating emotional responses in humans or other subjects.

Records of stimuli are accessed 502. The records record stimuli provided to the subject while the fMRI data was collected. In diagnostic data, correspondences between provision of stimuli and the changes in emotional state in the brain are recorded 504. For example, the computer system 108 can access historical records for the subject that include a table of stimuli, intensity, and duration that are provided to the subject. This table can then be augmented with data from the tables 204 and/or 206 to record how those stimuli influenced the subject.

One of the stimuli is selected for future exposure to the subject based on the recorded correspondences 506. For example, a researcher or clinician may determine that it is appropriate to elicit a particular emotion, and may look up the stimuli that have historically elicited that emotion from the subject. Then, the researcher or clinician may apply that stimuli.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A system for generating diagnostic data from medical imaging, the system comprising:
   one or more computers and one or more storage devices on which are stored instructions that are operable, when executed by the one or more computers, to cause the one or more computers to perform operations comprising:
   accessing fMRI data of a subject brain comprising a plurality of time-sequenced volumetric images of activity in a subject brain;
   accessing a plurality of emotion vectors, each emotion vector tagged with a specified emotional state;
   determining, from the fMRI data and using the emotion vectors, a plurality of fMRI state vectors at various points in time, where each fMRI state vector is a combination of the emotion vectors and represents the state of the subject brain at a particular point in time;
   determining flow data to identify a trajectory, over time, of the subject brain as reflected by the fMRI data, through a state space defined by the emotion vectors, wherein the flow data is based at least in part on the fMRI vectors at various points in time; and
   generating, from the flow data, data that shows changes, through time, in at least one emotional state of the brain.

2. The system of claim 1, the operations further comprising accessing records of stimuli provided to the subject while the fMRI data was collected; and
   recording, in the diagnostic data, correspondences between provision of stimuli and the changes in emotional state in the brain.

3. The system of claim 2, the operations further comprising selecting one of the stimuli for future exposure to the subject based on the recorded correspondences.

4. The system of claim 1, the operations further comprising recording in the diagnostic data a resting emotional state for the subject based on the changes in emotional state of the brain.

5. The system of claim 1, the operations further comprising providing the diagnostic data to a recommendation engine configured to receive the diagnostic data and provide one or more recommendations for interventions for the subject.

6. The system of claim 5, wherein the recommendation is one of the group comprising a drug intervention, and a behavioral intervention.

7. The system of claim 1, wherein the plurality of emotion vector comprises thirty-four emotion vectors.

8. The system of claim 7, wherein the emotions comprise sexual desire, aesthetic appreciation, entrancement, disgust, amusement, fear, interest, anxiety, surprise, joy, horror, adoration, calmness, romance, awe, nostalgia, empathic pain, relief, awkwardness, craving, excitement, sadness, boredom, triumph, sympathy, admiration, anger, satisfaction, confusion, disappointment, pride, envy, contempt, and guilt.

9. The system of claim 1, each emotion vector storing values reflecting average brain activity for other brains that have experienced the specified emotional state.

10. The system of claim 1, wherein the operations further comprise:
    accessing training-fMRI data for a plurality of other brains, the plurality of other brains not including the subject brain;
    aggregating the training-fMRI data to find common functional data across the training-fMRI data; and
    storing the common functional data as the plurality of emotion vectors.

11. The system of claim 10, wherein accessing fMRI data of a subject brain is performed after storing the common functional data as the plurality of emotion vectors.

12. A method for generating diagnostic data from medical imaging, the method comprising:
    or more computers to perform operations comprising:
        accessing fMRI data of a subject brain comprising a plurality of time-sequenced volumetric images of activity in a subject brain;
        accessing a plurality of emotion vectors, each emotion vector tagged with a specified emotional state;
        determining, from the fMRI data and using the emotion vectors, a plurality of fMRI state vectors at various points in time, where each fMRI state vector is a combination of the emotion vectors and represents the state of the subject brain at a particular point in time;
        determining flow data to identify a trajectory, over time, of the subject brain as reflected by the fMRI data, through a state space defined by the emotion vectors, wherein the flow data is based at least in part on the fMRI vectors at various points in time; and
        generating, from the flow data, data that shows changes, through time, in at least one emotional state of the brain.

13. The method of claim 12, the method further comprising accessing records of stimuli provided to the subject while the fMRI data was collected; and
    recording, in the diagnostic data, correspondences between provision of stimuli and the changes in emotional state in the brain.

14. The method of claim 13, the method further comprising selecting one of the stimuli for future exposure to the subject based on the recorded correspondences.

15. The method of claim 12, the method further comprising recording in the diagnostic data a resting emotional state for the subject based on the changes in emotional state of the brain.

16. The method of claim 12, the method further comprising providing the diagnostic data to a recommendation engine configured to receive the diagnostic data and provide one or more recommendations for interventions for the subject.

17. The method of claim 16, wherein the recommendation is one of the group comprising a drug intervention, and a behavioral intervention.

18. The method of claim 12, wherein the plurality of emotion vector comprises thirty-four emotion vectors.

19. The method of claim 18, wherein the emotions comprise sexual desire, aesthetic appreciation, entrancement, disgust, amusement, fear, interest, anxiety, surprise, joy, horror, adoration, calmness, romance, awe, nostalgia, empathic pain, relief, awkwardness, craving, excitement, sadness, boredom, triumph, sympathy, admiration, anger, satisfaction, confusion, disappointment, pride, envy, contempt, and guilt.

20. The method of claim 12, each emotion vector storing values reflecting average brain activity for other brains that have experienced the specified emotional state.

* * * * *